United States Patent [19]
Hughes

[11] Patent Number: 5,494,598
[45] Date of Patent: Feb. 27, 1996

[54] HEAT EXCHANGE MEDIUM AND ARTICLES FOR USE THEREOF

[75] Inventor: Thomas E. Hughes, Cedar Mountain, N.C.

[73] Assignee: Thermionics Corporation, Springfield, Ill.

[21] Appl. No.: 227,092

[22] Filed: Apr. 13, 1994

Related U.S. Application Data

[63] Continuation of Ser. No. 888,553, May 22, 1992, abandoned, which is a continuation-in-part of Ser. No. 705,536, May 24, 1991, abandoned.

[51] Int. Cl.$^6$ .............................. C09K 5/06; H05B 6/64; A61F 7/02; A45D 2/36
[52] U.S. Cl. ................. 252/70; 165/10; 219/759
[58] Field of Search ................. 252/70; 165/10 A; 219/10.55 F, 10.55 R, 759

[56] References Cited

U.S. PATENT DOCUMENTS

| | | | |
|---|---|---|---|
| 4,253,983 | 3/1981 | Blanie | 252/70 |
| 4,538,630 | 9/1985 | Henderson | 132/33 R |
| 4,743,726 | 5/1988 | Hughes et al. | 219/10.55 F |
| 4,849,593 | 7/1989 | Hughes et al. | 219/10.55 R |

FOREIGN PATENT DOCUMENTS

| | | |
|---|---|---|
| 2003285 | 5/1990 | Canada . |
| 1452833A | 6/1986 | U.S.S.R. . |
| 90/05508 | 5/1990 | WIPO . |

OTHER PUBLICATIONS

Akira, Thermal Storage Agent, Feb. 25, 1991, Japan 23002489.
Toppan, Latent Heat Accumulator Compositions with Prolonged Life, Jan. 12, 1983, Japan, 58005386.
Hitec, Heat Storage Material with Heater Using It, Feb. 19, 1992, Japan, 4050285.
Patent Abstracts of Japan, Dec. 14, 1990, JP2302489.
World Patents Index Latest/Derwent, Jan. 23, 1989, 89"322262, SU 1452833.
World Patents Index Latest/Derwent, Jan. 12, 1983, 83–18414K JP 58–5386.
World Patents Index Latest/Derwent, Feb. 19, 1992, 92–109248, JP 4–50285.

*Primary Examiner*—Christine Skane
*Attorney, Agent, or Firm*—Dority & Manning

[57] ABSTRACT

A novel heat exchange medium made from a clay and oil mixture for use in absorbing, retaining, and dispensing heat is provided. The composition and variations thereof are most effective when heat treated so as to reduce the expansion of gases when the composition is encapsulated in sealed packaging. Particularly, the composition may employ microwave heatable and/or microwave invisible clays in combination with microwave invisible oils, such as mineral oils or microwave heatable oils, such as vegetable oils. Various constituents may be added to the medium, such as fibers made of polymeric substances and/or cloth, moisture absorbents such as polyacrylamide, and plastics such as polypropylene and the like. Various applications of the heat exchange medium are provided and are specifically directed to industrial heat exchange applications and domestic items such as hair rollers, heating pads, heating packs, including a booster-type pack with varying levels of thermal capabilities, and heat exchange medium-coated fibers.

6 Claims, 2 Drawing Sheets

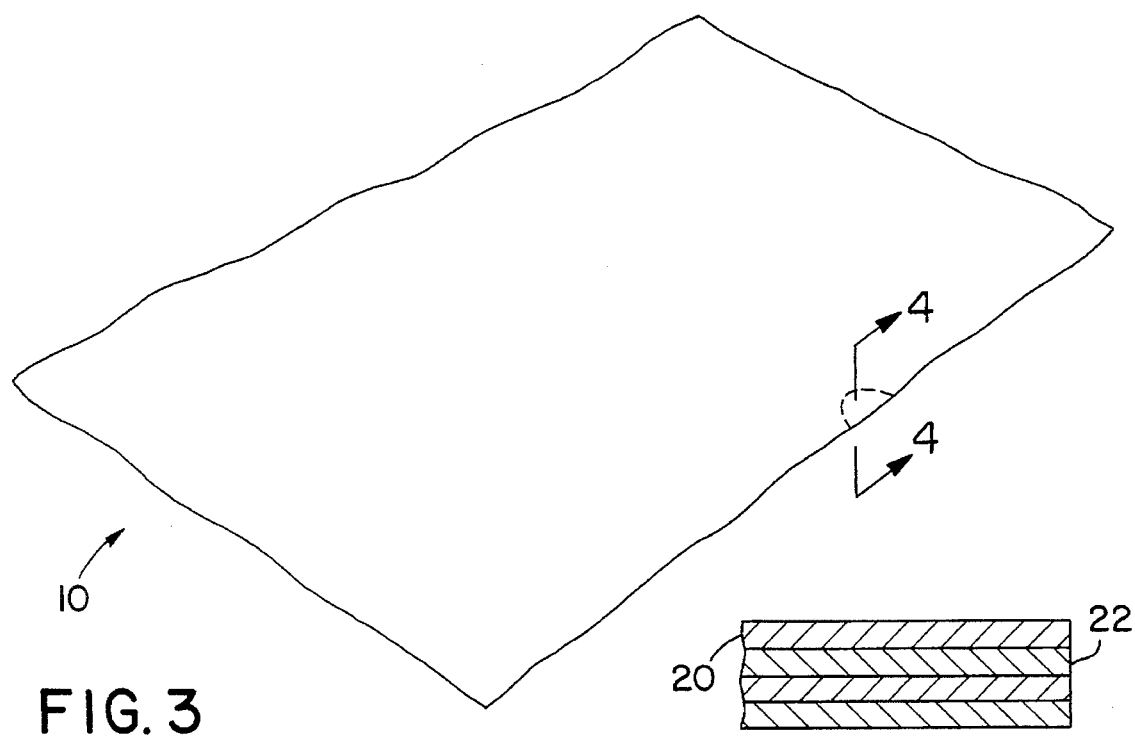
FIG. 3
FIG. 4
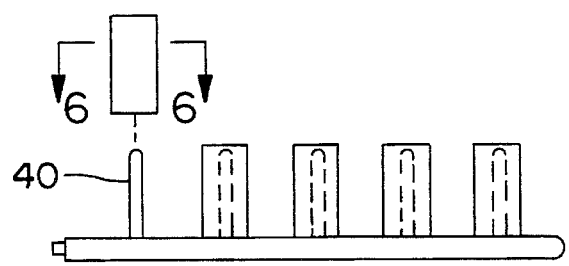
FIG. 5
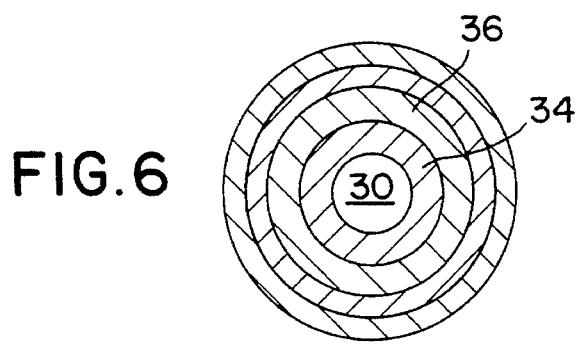
FIG. 6

HEAT EXCHANGE MEDIUM AND ARTICLES FOR USE THEREOF

BACKGROUND OF THE INVENTION

This is a continuation of application U.S. Ser. No. 07/888,553, filed May 22, 1992, which was abandoned upon the filing hereof, which application is a continuation-in-part of U.S. Ser. No. 07/705,536 filed May 24, 1991, now abandoned, which is fully incorporated herein by reference.

FIELD OF THE INVENTION

This invention relates to a heat exchange medium made from clay and oil and to use of the heat exchange medium to make various articles therefrom.

Many thermal storage mediums capable of transferring heat and cold have been employed for absorbing, containing, storing, and releasing heat. Various ice-pack-like products and other insulators have been utilized to absorb and release heat to foods, the human body, and other applications.

For example, U.S. Pat. No. 4,253,983 to Blanie discloses a thermally conductive paraffin composition used as a shapeable heat casing element for storing and releasing heat. The thermal properties may be improved by incorporating therein finely divided metals, their oxides, or their silicates. Various therapeutic applications for such compositions are described in the '983 patent.

Another heat exchange medium is described in Soviet Union Patent No. 1452-833-A. The composition described therein comprises powdered clay in an amount of 83 to 85 percent and industrial oil in an amount of 15 to 17 percent. The components are mixed together and coated onto the foundation of buildings to prevent frost deformation and freeze-adhesion of moist substances.

PCT application Publication No. WO90/05508 discloses a heating pad having an inner pouch and an outer cover. The inner pouch encloses a heat retaining liquid with granules of comminuted polyurethane foam material therein. The polyurethane granules store heat when the liquid is heated and the heating pad gives off warmth thereafter. The material may be heated by microwaves. The liquid generally comprises a heat retaining base material formed from gel, wax or oil such as paraffin wax, or vegetable, mineral or animal oils. The material may also comprise a mixture of ethylene or propylene glycol and methyl cellulose, as well as various other additives.

U.S. Pat. Nos. 4,743,726 and 4,849,593, which were invented by the present inventor, also disclose heat exchange mediums. The '726 patent discloses a microwave-activated heating element comprising a water saturated cellular core, water, a heat and flame resistant rubber coated with a high temperature lubricant, and a wax center core therein to absorb and store heat from the microwave heatable water and rubber component. The construction of the heating element may be concentrically wound, tubular, layered, or sectioned particles as necessary to conform to the specific design of the appliance in which the heating element is to be used. The patent describes a number of example applications such as hair rollers, curling irons, food warmers, and heating pads.

The '593 patent discloses another microwave-activated heating element in various forms. In one particular form, the heating element includes a multi-layered cartridge having a center core for dissipating heat, a layer of material reactive to microwaves for retaining heat, and an outer layer of paper for sealing the cartridge but allowing heat to radiate therefrom. In another form, the heating element has multiple rubber and cellular water retaining layers disposed about a central core of wax material. Another form described therein discloses a heating element comprising clay disposed within a covering and including various components such as water or oil. Rubber particles and high temperature lubricants may also be added to the microwave heatable clay/oil mixture for enhancing the heat retention aspects thereof.

Presently, many heat and cold transfer mediums employ materials such as petroleum, synthetically formulated hydrocarbons, silicones, and various other potentially harmful chemicals. Concerns have been raised about the improper use and disposal of the sometimes toxic and environmentally unsafe materials. The materials may be carcinogenic, may produce gases or other harmful agents, are generally expensive to manufacture, and require considerable energy during the process of absorbing sufficient heat. Such prior compositions also suffer from rapid dissipation of the stored heat or cold. Moreover, many of the prior art mediums are in a low viscosity liquid or fluid form and must be maintained in elaborate sealed containment vessels or contained within circulatory means such as pressurized piping systems.

Although the prior art shows various combinations of materials for retaining and exchanging heat, the particular features of the present invention are absent therefrom. The prior art is generally deficient in affording a non-toxic, biodegradable, environmentally safe, recyclable composition that, when combined in proper proportions and subjected to heat treatment, may be made into various solid, flexible, and viscous forms for acting as heat reservoirs and exchange mediums. The present invention overcomes the shortcomings of the prior art in that a heat exchange medium is disclosed that safely and effectively stores and transmits heat and cold in various articles.

SUMMARY OF THE INVENTION

It is an object of the present invention to provide a heat exchange medium comprising clay and oil which is non-toxic and environmentally safe but maintains and transfers heat and cold over a wide range of temperatures.

It is another object of the present invention to provide a heat exchange medium that has been heat treated to remove gases and moisture therefrom and to result in a flexible, moldable substance that remains cooler and maintains heat for a longer period of time than a non-heat treated composition.

It is further another object of the present invention to provide various articles made from a heat treated heat exchange medium comprising clay and oil.

It is another object of the present invention to provide cloth and polymeric fibers coated with a heat exchange medium comprising clay and oil.

It is another object of the present invention to provide a heat exchange medium having a moisture absorbent therein to decrease the amount of gas expansion when heated, the extent of water freezing when cooled, and the extent of separation of the composition when encapsulated.

It is another object of the present invention to provide articles having alternating layers of microwave heatable and microwave transparent heat exchange mediums made from clay and oil.

Another object of the present invention is to provide various articles, including building materials, solar energy collectors, root zone insulators, food warmers and coolers, electrical insulators, and other commercial products employing a heat exchange medium comprising clay and oil that may be heat treated.

It is another object of the present invention to provide a sealing agent comprising clay and oil.

It is further another object of the present invention to provide a removable and replaceable booster-type pack comprising clay and oil which may be placed in conductive relationship with a heat exchange medium comprising clay and oil that has different properties.

Generally speaking, the present invention is directed to a composition comprising clay and oil used to produce various articles for absorbing, retaining, and dispensing heat. The heat exchange composition is preferably heat treated to provide a medium with increased heat retention, as well as decreased moisture and gas constituents. Heat treating of the present heat exchange medium also renders the composition electrically non-conductive and sufficiently solid to allow shaping and molding thereof.

The properties of the heat exchange medium may be further modified by adding various components thereto, including moisture absorbents, such as polyacrylamide, to further decrease the potential for gaseous expansion within closed packaging. Moreover, the composition may have cloth or polymer fibers, such as polypropylene, added thereto to produce various articles of manufacture.

The heat exchange medium also functions extremely well when used in combination with other heat exchange mediums to produce heatable and coolable products having unique characteristics. Furthermore, the present heat exchange medium is useful for producing composites having alternating layers of microwave heatable and microwave transparent mediums. Various articles, such as hair rollers, heating pads, food warmers and coolers, root zone pads for horticultural applications, solar energy collectors, insulating blankets, heat retention liners, floor and wall heat retaining structures, therapeutic devices, electrical insulators, and substrates for electronic circuit boards can be produced from the present heat exchange medium.

Specifically, the heat exchange medium is composed of a basic clay and oil mixture. The clay is generally present in an amount of from about 25 percent to about 85 percent and the oil or other constituents are present in amounts of from about 15 percent to about 75 percent. Various types of clays can be used as well as various types of oils. In a preferred form, the clay/oil composition is heat treated at temperatures of from about 325° F. to about 425° F. for a period of from about 30 to about 60 minutes. The heat treating process renders the composition increasingly plasticized which results in superior moldability characteristics even at temperatures below −20° F. Moreover, the heat treating process allows the heat exchange composition to remain 15 to 20 percent cooler, to store heat 15 to 20 percent longer, and to produce 85 to 95 percent less moisture and gases than the composition if not subjected to heat treatment.

The present invention eliminates the need for special handling and disposal procedures that are often involved with other heat exchange mediums. The present invention also avoids using limited natural resources, such as petroleum-based ingredients. Clay is relatively plentiful and readily available at low cost. It is safe and easy to produce, store, and distribute, and is completely safe to handle. Moreover, the present heat exchange composition is recyclable and cleans up effectively with soap and water until after it is heat treated.

BRIEF DESCRIPTION OF THE DRAWINGS

A full and enabling disclosure of the present invention, including the best mode thereof, to one of ordinary skill in the art, is set forth more particularly in the remainder of the specification, with reference to the accompanying figures, in which:

FIG. 3 is a perspective view of a blanket or liner made in accordance with the present invention;

FIG. 4 is a view along line 4—4 of FIG. 3 showing a cross section of a blanket or liner material in accordance with the present invention;

FIG. 5 is a side view of a heatable hair roller system in accordance with the present invention; and FIG. 6 is a view along line 6—6 of FIG. 5 showing a cross section of a hair roller in accordance with the present invention.

Figure 1:
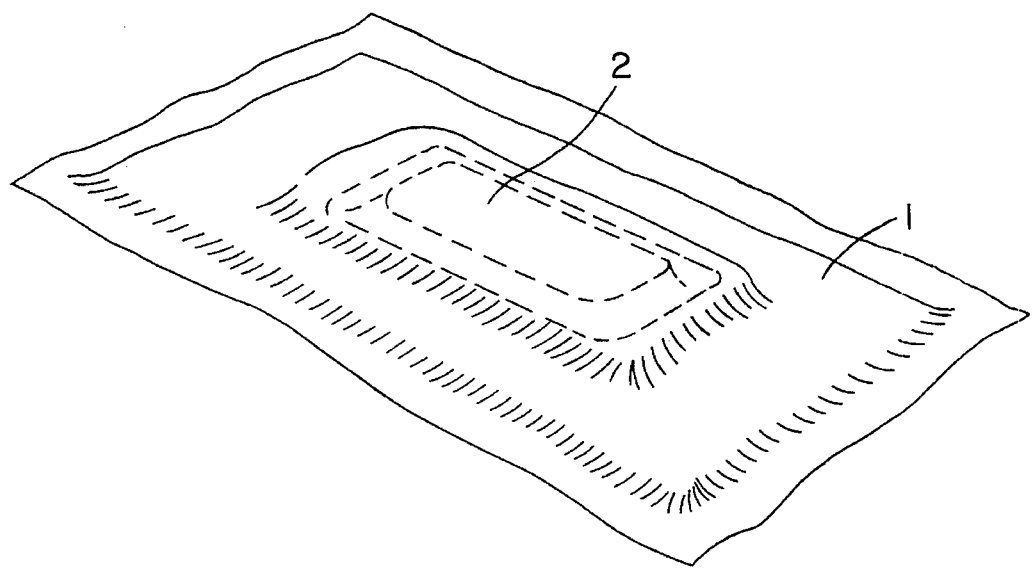
FIG. 1 is a perspective view of a booster pack-type heating element in accordance with the present invention.

Repeat use of reference characters in the present specification and drawings is intended to represent same or analogous features or elements of the invention.

DESCRIPTION OF PREFERRED EMBODIMENTS

A composition employed as a heat exchange medium is provided. Generically, the basic composition comprises a mixture of clay and oil. The clay is present in an amount of from about 25 percent to about 85 percent and the oil or other constituents are present in an amount of from about 15 percent to about 75 percent. The actual percentages are based on the characteristics and properties desired relative to the chosen application of the heat exchange medium. Generally, a higher clay content results in a more viscous and solidified material whereas a higher oil content results in a more fluid and flowable heat exchange medium.

Preferably, the heat exchange composition is heat treated to achieve unique and desirable properties. The heat treated composition results in a solidified and cohesive composition that is substantially more workable than the basic clay/oil composition. The heat treated medium is moldable and the oil in the mixture is not as easily separable from the clay. If not heat treated, the oil in the basic clay/oil composition tends to separate.

The heating process removes various impurities that may be present in the clay/oil composition. Removal of impurities is particularly important when the heat exchange medium requires sterilization for use in health care and other therapeutic applications.

Heat treating also removes various gas producing elements. When the basic clay/oil medium is encapsulated and heated in a sealed containment vessel, generally a plastic such as polyethylene or polypropylene, a popping sound is heard at about 300° F., indicating the presence of expanding gases within the vessel. Such expansion of gases results in structural stresses on the encapsulating containment vessel with the end result being a leak of the composition outside the packaging. Heat treatment removes a substantial portion of the moisture and gas producing constituents so that the resulting heat treated heat exchange medium may be heated numerous times without failure of the encapsulating compartment.

A further benefit of heat treating is that the basic clay/oil composition then becomes dielectric, or non-electrically conductive. This characteristic allows the heat treated composition to be used as an electrical insulator in various applications. One such application is to replace the oil-based substances currently employed in many electrical transformers with the present heat treated medium. The heat treating process removes substantially all of the electrolytes found within the composition.

Although heat treating is most preferred within the range of 325° F. to 425° F. for 30 to 60 minutes, various other temperatures and lengths of time can be used to heat treat the composition to achieve various desired characteristics. The extent of heating also depends on how the heat treating process is effectuated. For example, if microwaves are being used to heat treat the composition, cycling of the microwave heating may be necessary so that excessive temperatures are minimized.

A further benefit of the heat treated composition is that it results in a heat exchange medium allowing for a more rapid spread of microwaves throughout the medium than that found in the basic clay/oil composition. In other words, the heat conduction, or thermal diffusivity, of the heat exchange medium is enhanced by the heat treatment. In addition to the heat treated heat exchange medium remaining 15 to 20 percent cooler, heat retention is improved by 15 to 20 percent. Either cold or heat, depending on which is being retained, is retained 15 to 20 percent longer in the heat treated composition than in the basic clay/oil composition.

Heat treating of the composition permanently changes the medium. Further heat treating and/or cooling does not result in a reversion of the composition to its initial free-flowing form. One particularly beneficial aspect of heat treating the composition is that the heat treated composition remains flexible even at temperatures below −20° F. The heat treating of the composition does not, however, decrease the medium's ability to be cooled and heated in indefinite repeated cycles from below −20° F. through and above 675° F.

The present invention may be better understood by reference to the following examples and described embodiments.

EXAMPLE 1

To form the basic clay/oil composition of the present composition, a dry, fine, preferably 60–200 mesh, clay material is mixed with a vegetable oil in a proportion of approximately one part oil to three parts clay. The oil may be derived from any vegetable, such as soybeans, and the clay in this particular embodiment is a microwave reactive clay such as that described below. Vegetable oil is microwave reactive, which means that it also may be heated by microwaves. The basic composition, however, may also be heated by other conventional means including gas, electrical, steam, hot water, solar, and the like. The composition, when exposed to various cooling agents such as refrigeration appliances, refrigerants, dry ice or other cold transfer mediums, will absorb, store, contain and transfer the cold temperatures. The composition forms an extrudable, pliable medium for heat and cold that exhibits a broad range of temperature storage capabilities from below −20° F. through about 375° F. The clay material used in the present composition is a mixture of the constituents listed below:

| | |
|---|---|
| Silica (SiO$_2$) | 55.78–64.00% |
| Alumina (Al$_2$O$_3$) | 16.00–28.34% |
| Iron Oxide (Fe$_2$O$_3$) | 1.50–7.50% |
| Titania (TiO$_2$) | 1.50–1.67% |
| Magnesia (MgO) | 0.34–1.55% |
| Calcium Oxide (CaO) | 0.18–0.22% |
| Sodium Oxide (Na$_2$O) | 0.22–0.40% |
| Potassium Oxide (K$_2$O) | 1.68–4.07% |

EXAMPLE 2

In another embodiment, the clay/oil composition may incorporate a form of clay known as bentonite. In this particular embodiment, 15 to 20 percent of the clay base material employed in Example 1 is replaced with a like amount of bentonite clay. Bentonite is also microwave reactive, maintaining the capability of the clay component of the medium to be heated in a microwave. Use of bentonite in the composition also results in a heat exchange medium exhibiting better plasticity and moldability. The bentonite clay used has the following constituents:

| | |
|---|---|
| Silica (SiO$_2$) | 58.00–64.00% |
| Alumina (Al$_2$O$_3$) | 18.00–21.00% |
| Iron Oxide (Fe$_2$O$_3$) | 2.50–2.80% |
| Magnesia (MgO) | 2.50–3.20% |
| Lime | 0.10–1.00% |
| Soda | 1.50–2.70% |
| Potash | 0.20 |

A comparison of water and the heat treated form of the bentonite-containing heat exchange composition of Example 2 was conducted. At 77° F., the viscosity of the heat exchange medium was 45 poise and the density was 15 pounds per gallon, compared to water which has a viscosity of 1 centipoise and a density of 8 pounds per gallon. The freezing point of water is 32° F. and the freezing point of the heat exchange composition was found to be −44° F. The specific gravity of water is 1 gram per milliliter and the specific gravity of the heat exchange medium was found to be 1.78 grams per milliliter. The specific heat of water is 4.2 kj/kg°C. and the specific heat of the heat exchange medium was found to be 2.5 kj/kg°C.

Various plastic encapsulated containers of the heat exchange medium produced in accordance with Example 2 were formulated. The packs were heated and cooled as specified in Table I. Table I represents the amount of heat or cold retention after certain periods of time.

TABLE I

| SAMPLE # | 1 | 2 | 3 |
|---|---|---|---|
| HOT PACK - CORE TEMPERATURE | | | |
| Size of Pack | 9½" × 16" | 6" × 12" | 4" × 18" |
| Weight | 3 lb. | 1½ lb. | 1½ lb. |
| Microwave Heat Time At 600 Watts | 3 min. | 2 min. | 2 min. |
| Initial Temp. | 172° F. | 160° F. | 160° F. |
| After 20 Minutes | 152° F. | 150° F. | 149° F. |
| After 30 Minutes | 140° F. | 145° F. | 135° F. |
| After 40 Minutes | 138° F. | 138° F. | 130° F. |
| After 60 Minutes | 130° F. | 130° F. | 125° F. |
| After 90 Minutes | 114° F. | 118° F. | 110° F. |
| COLD PACK - CORE TEMPERATURE | | | |
| Size | 9½" × 16" | 6" × 12" | 4" × 18" |

TABLE I-continued

| SAMPLE # | 1 | 2 | 3 |
|---|---|---|---|
| Weight | 3 lb. | 1½ lb. | 1½ lb. |
| Freezer Temperature | 7° F. | 7° F. | 7° F. |
| Initial Temp. | 3° F. | 3° F. | 3° F. |
| After 20 Minutes | 9° F. | 9° F. | 16° F. |
| After 30 Minutes | 14° F. | 15° F. | 22° F. |
| After 40 Minutes | 18° F. | 20° F. | 26° F. |
| After 60 Minutes | 25° F. | 28° F. | 32° F. |
| After 90 Minutes | 35° F. | 39° F. | 51° F. |

EXAMPLE 3

In another embodiment, the microwave heatable vegetable oil is replaced by a microwave invisible substance such as mineral oil. (As used herein, the term microwave invisible refers to the lack of an ability to be heated by microwaves.) The resulting composition exhibits a more rapid absorption of heat and is particularly useful in various kitchen and food service applications, personal care devices, health and beauty applications, and heating and air conditioning units.

EXAMPLE 4

A further variation of the present heat exchange medium allows for decelerated heat absorption by using a non-microwave heatable clay base material. One such clay that is not microwave heatable is kaolin. In this particular embodiment, kaolin is substituted for the clay described in Example 1 and a decreased heating of the composition is achieved. This particular form of the composition is particularly useful when the heat exchange medium absorbs heat from a source other than high frequency microwaves. Kaolin generally has the following constituents:

| Silica ($SiO_2$) | 46.50% |
|---|---|
| Alumina ($Al_2O_3$) | 37.62% |
| Iron Oxide ($Fe_2O_3$) | 0.51% |
| Titania ($TiO_2$) | 0.36% |
| Magnesia (Mgo) | 1.55% |
| Calcium Oxide (CaO) | 0.25% |
| Sodium Oxide ($Na_2O$) | 0.02% |
| Potassium Oxide ($K_2O$) | 0.40% |
| Potassium ($P_2O_5$) | 0.19% |
| Sodium (Na) | 0.21% |

Other various constituents may be added to the basic clay/oil compositions of Examples 1–4, including hardening agents. Such hardening agents are also known as plasticizers and are well known for their ability to solidify compositions. Hardening agents should be chosen that are heat and cold resistant so that the agents are not degradated by constant heating and cooling thereof.

EXAMPLE 5

In a preferred form of the invention, the heat exchange composition is subjected to heat treatment as described above. Particularly, any of the clay/oil compositions described in Examples 1–4 can be heat treated to attain such a medium. The process of heat treating the composition involves heating the clay/oil basic composition to a temperature in the range of from about 325° F. to about 425° F. for a period in the range of from about 30 minutes to about 60 minutes. The heat treating process can be effectuated by heating the composition in any heatable vessel, or while being extruded, by any heating means, including microwaves, gas, electrical, and the like. During the heat treating process, the clay/oil composition is preferably stirred or turned so that heat is transmitted throughout the composition.

EXAMPLE 6

The clay/oil composition of Example 1 was heated as described in Example 5 at 375° F. for a period of about 60 minutes. A semi-soft, flexible heat exchange medium was produced thereby.

EXAMPLE 7

The clay/oil composition of Example 1 was heated as described in Example 5 at 475° F. for a period of about 30 to 40 minutes. A semi-hard, semi-flexible product was produced thereby.

EXAMPLE 8

The clay/oil composition of Example 1 was heated as described in Example 5 at about 575° F. for a period of about 30 minutes. A hardened, unflexible product was produced thereby.

EXAMPLE 9

The clay/oil composition of Example 1 was heated as described in Example 5 at about 675° F. for a period of about 40 minutes to one hour. A very hard brick-like product was produced thereby.

Any of the heat treated compositions described in Examples 5–9 may be employed as a heat exchange medium in various articles and for various applications. The mediums of Examples 5–9 are capable of being molded and formed, and therefore, may be used in various shapes, thicknesses, sizes and hardnesses for heat absorption, storage, and transmission. Such uses include the formation of molded solid and semi-solid insulating blankets, solar energy collectors, heat or cold retention liners, food warmers and/or coolers, building structures capable of maintaining heat and having insulation characteristics such as floor and wall area covers and bricks, coatings for various substrates such as sheetrock and plaster, various therapeutic and orthopedic heat/cold devices for both humans and animals, electrical insulators, and substrates for use in producing electronic circuit boards where heat retention or dissipation is necessary.

In another particular embodiment of the present invention, woven, non-woven, and loose fibers made of various materials may be added to the heat treated medium of Examples 5–9 and/or the basic clay/oil compositions of Examples 1–4. The addition of fibers strengthens the composition and provides for further molding capabilities. Additionally, electrically conductive fibers may be added to transform the dielectric composition into an electrically conductive composition.

The fibers may be added to the compositions during the heating process or afterwards while the composition is still hot. Adequate dispersion of the fibers throughout the composition may be achieved by mixing or hand laying of the fibers.

Fibers may be added fibers in the form of wraps, sheets, and mats of various thicknesses and sizes. The fibers may be fibers of cloth or polymeric fibers, such as polypropylene fibers. Other fibers that may be utilized include graphite, textiles, other polymeric fibers, fiberglass fibers, ceramic fibers, or even fibers comprising the clay/oil composition described herein.

When fibers are added in the flexible roll form, the fiber-treated composition can be used in applications requiring an effective sealant against water, solvents, toxic waste, landfill leaching and the like. Such practical applications for use of the heat exchange medium with fibers immersed therein include roofing, basement sealers, landfill sealers, pond sealers and roadbed sealers. The composition of the present invention is impermeable to various organic solvents, including alcohol, acetone and ether. The composition is also impermeable to water.

Another desired property resulting from fiber immersion within the composition is the increased uniformity of thermal diffusivity throughout the heat exchange medium. Like heat treatment, fibers tend to spread the heat or cold throughout the medium more evenly.

Heat treating described above may be applied before or after the fibers are impregnated into the composition. The composition may alternatively be cured in warm, dry air. For sealing applications such as those described above, air drying allows the fiber-impregnated composition to more effectively mold and seal to the area of application. Air drying may also be more cost and energy efficient than supplying heat by other means.

Adding polypropylene or other polymeric substances to the composition allows for manufacture of plastic articles having the capability of absorbing, retaining and dispensing heat. Polypropylene does not substantially affect the cold/heat retention characteristics of the composition and is also microwave invisible. Other various polymeric substances which may be used include any of the plastics such as polytetrafluoroethylene and polyethylene. Although in the example described herein, one part of polymer is combined with three parts of the clay/oil composition, such proportions are not critical to the invention.

In another form, polypropylene may be added to the clay/oil composition during the heat treating process. In one particular embodiment, one part polypropylene powder was combined with three parts of the clay/oil composition described in Example 1. The clay/oil/polymer composition produced thereby may then be extruded into fibers and molded into various articles. The fibers formed thereby may be used as sheeting, mats, textile products, insulation, and may also be molded to form microwave heatable products. One such composition employing polypropylene was cooled as low as $-20°$ F. and heated up to $225°$ F. and exhibited substantially longer cold and heat retention than the composition without the polymeric fibers.

In another particular embodiment, a moisture absorbent may be added to the basic clay/oil compositions of Examples 1–4 or the heat treated versions of the composition described in Examples 5–9. One such moisture absorbent for use in the present invention is polyacrylamide. Moisture absorbents reduce the gas producing constituents to thereby lessen the possibility of gaseous expansion within the packaging. Moisture absorbents having the ability to operate within the temperature ranges of the present invention may be employed. Polyacrylamide is a preferred moisture absorbent because it is operational in a temperature range from $-40°$ F. to $400°$ F.

In one particular mixture of the present invention with a moisture absorbent, 16 ounces of the basic clay/oil composition described in Example 1 was mixed with two ounces of water-impregnated polyacrylamide. Water-impregnated polyacrylamide was initially made by combining two ounces of water with three grams of dry, 200 mesh (0–500 micron size), powdered polyacrylamide. The water-impregnated polyacrylamide is added to the present composition in the form of a gel-like material. This particular composition acts as a low temperature reservoir for cold temperatures down to $-60°$ F.

Another form of the moisture absorbent/clay/oil composition that prevents solid freezing and formation of ice crystals, utilizes alcohol or propylene glycol to replace 25 percent of the water in making the water-impregnated polyacrylamide. Specifically, for applications within a temperature range between $0°$ F. and $32°$ F., 25 percent of the water used in making the water-impregnated polyacrylamide described above is substituted with a like amount of alcohol or propylene glycol. At operational temperatures below $0°$ F., up to about 50 percent of the water may be replaced in the water-impregnated polyacrylamide with propylene glycol. When substituting alcohol or propylene glycol for water, the polyacrylamide powder must be mixed with the water first and then the alcohol or propylene glycol must be added thereto.

The resulting heat exchange medium employing the moisture absorbent increases the cold retention characteristics of the clay/oil composition by creating a suspension in which oil and water combine with the clay to function as a cold to hot reservoir. This particular medium allows oil and water to mix without tending to separate.

In another embodiment employing a moisture absorbent, 0.5 ounces of dry, 200 mesh polyacrylamide powder was combined with 16 ounces of the basic clay/oil composition of Example 1. The composition was formed into a heat exchange medium and encapsulated within a plastic package. The clay/oil mixture in combination with the moisture absorbent did not produce substantial gases when it was heated above $275°$ F. Accordingly, any potential for seal failure of the encapsulating package is lessened by use of the moisture absorbent. A water-soaked and frozen heat exchange medium of same also remained frozen 2.4 times longer than frozen water alone.

Figure 2:
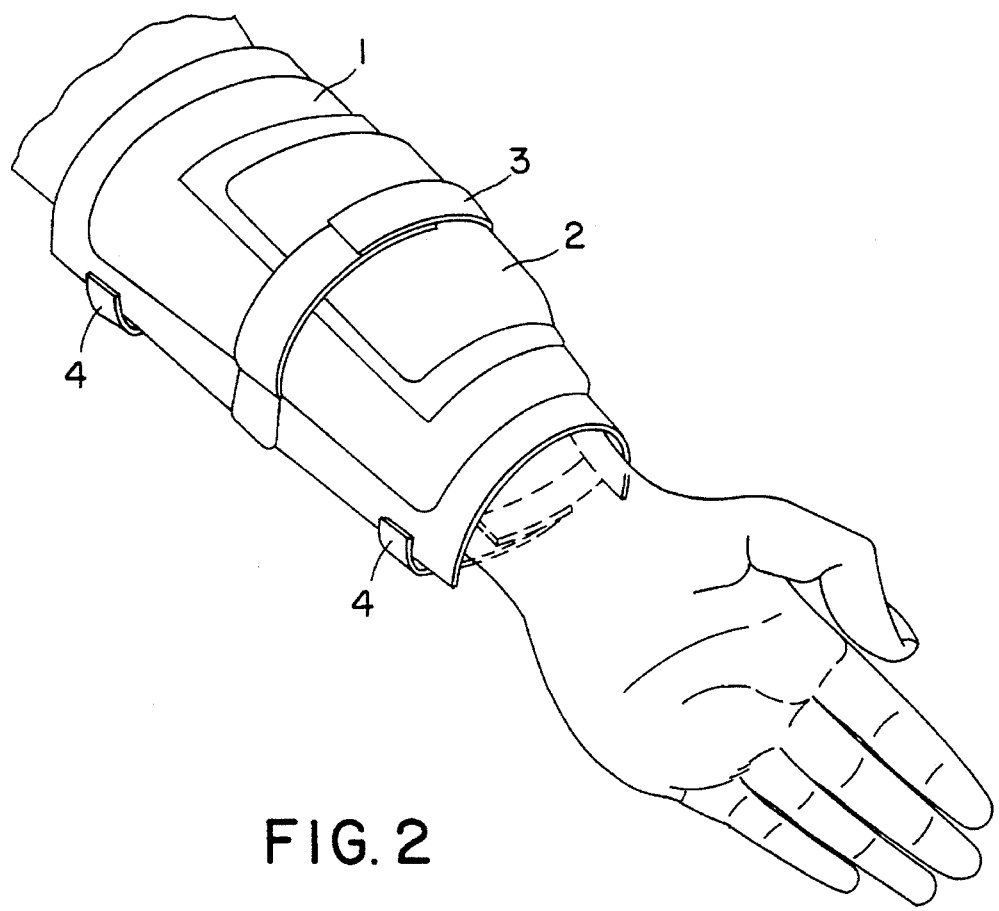
FIG. 2 is a perspective view of a booster pack-type heating element in use in accordance with the teachings of the present invention.

The present invention may also employ a booster pack within an encapsulated pack of the basic clay/oil or heat treated clay/oil composition as shown in FIGS. 1 and 2 as described below. A "booster" pack of the clay/oil composition may be made in either heat treated or non-heat treated form. The booster package should exhibit a different thermal capability than the clay/oil composition package within which the booster pack maintains contact. Preferably, the booster package contains the basic clay/oil composition as described in Examples 1–4 which is not heat treated. Preferably, the composition of the booster package contains polyacrylamide therein to provide the properties discussed above. The main vessel preferably contains the heat treated version of the composition made in accordance with Examples 5–9.

The booster package may be sealed inside of a larger containment vessel carrying another form of the present composition as in FIG. 1 or may be a separate vessel as shown in FIG. 2. By employing such a booster package form within a larger main pack, the cold retention and heat retention of the entire pack may exceed former retention times by 50 percent. Moreover, upon heating, temperatures remain lower in the main package than in the booster package attached thereto. A surrounding clay/oil composition acts as an insulator to preserve and retain the heat or cold within in the booster portion of the product and to provide for a substantially slower dissipation of the heat from the booster package.

As shown in FIG. 1, two separate encapsulated plastic packages 1 and 2 are shown. Encapsulated package 1 is the main vessel and preferably contains the heat treated version of the clay/oil composition made in accordance in the Examples 5–9. Encapsulated package 2 is the booster pack which is smaller than encapsulated package 1 and preferably contains the basic clay/oil composition described in Examples 1–4. In FIG. 1, encapsulated booster package 2 is shown as an integral portion of the main vessel encapsulated package 1. As described below, heat or cold treating of the arrangement, including both packages 1 and 2 results in more heat in the booster package 1. Encapsulated package one, containing the heat treated clay/oil composition can then maintain the heat or cold of booster package 1.

FIG. 2 shows another embodiment of the present invention wherein encapsulated package 2 (booster pack) is attached to encapsulated package 1 through a suitable securing means such as a velcro strap 3. In this embodiment shown in FIGS. 2, the booster pack 2 is removable and replaceable relative to the main vessel 1. The entire heating unit is then attached to a part of the body, or other structure, through use of other securing means such as velcro straps 4.

In operation, the entire pack, including the main package 1 with the heat treated composition therein and the booster pack 2 containing the non-heat treated composition attached thereto, either encapsulated within the main package 1 as shown in FIG. 1 or attached separately but in conductive relationship with at least a portion of the main package 1 as shown in FIG. 2, is heated or cooled as necessary. The booster portion of the heating or cooling element achieves higher temperatures and dissipates the heat or cold at a more rapid rate.

After the booster package 2 dissipates its heat or cold into the surrounding main pack 1, the booster package 2 in the embodiment shown in FIG. 2 may be removed and replaced with another booster package which has been either cooled or heated as needed. The resulting application allows main pack 1 to remain in place permanently, or at least for an extended period of time, while booster package 2 is removed and then reheated or recooled and then replaced into conductive relationship with main package 1. In this manner, booster package 2 is the only portion of the heating element all that is reheated or recooled.

One particular form of the booster/main package arrangement was tested on randomly selected patients who had undergone third molar odontectomies. Some of the patients who had undergone the oral surgery received an encapsulated main pack with booster pack separate therefrom but in a conductive relationship therewith as shown in FIG. 2, i.e., the booster pack was a separately encapsulated package which in use was merely secured or placed into contact with the main pack. Other patients received conventional ice packs. When using the packs of the present invention, the main pack remained on the patients' skin surrounding the location of the oral surgery for about eight hours. The small booster packs containing the non-heat treated composition of Example 1 was removed and cooled every one and half hours or as necessary.

The conventional ice packs only maintained sufficient cooling treatments for 20 to 40 minutes. As mentioned above, the booster package arrangement of the present invention allowed main pack 1 to maintain sufficient cooling properties during the entire eight hours, provided that the small booster pack 2 was replaced about every hour and a half.

Each of the patients using the thermal booster pack arrangement described herein rated the therapy a "4" on a scale of "1" to "5" with "5" being the best. When using the traditional ice packs, half of the patients rated the ice pack therapy as a "3". Patients commented that the thermal booster pack arrangement provided a much longer and more satisfying heat transfer than the conventional ice packs.

In another particular embodiment, the present invention may be employed in a blanket-type structure such as that shown in FIG. 3. This particular embodiment has alternating layers of microwave heatable and microwave transparent mediums as shown in FIG. 4. For example, an initial top layer 20 of a blanket generally indicated as 10, or other structure, may comprise a microwave transparent medium such as mineral oil and/or microwave invisible clay such as kaolin. The next layer 22 underneath top layer 20 may comprise a microwave reactive layer such as vegetable oil or bentonite clay. Layers thereunder may have alternating or successive microwave heatable and microwave invisible layers. Such microwave heatable clays include montmorillonite, kollinite, nacrite, dickite, holloysite and illite, in addition to the previously-described bentonite.

Hair rollers as shown in FIGS. 5 and 6 may also employ the present heat exchange medium. A fluid/air flow channel 30 in the center of concentric layers encapsulated by layers of the heat exchange mediums is provided. The center channel is preferably immediately encapsulated by a microwave heatable layer 34 of the bentonite/oil composition described in Example 2 and the next concentric layer 36 contains the clay/oil composition wherein kaolin, a microwave invisible clay, is employed. Such arrangements allow heating of the hair rollers to only 170° F. to 180° F. rather than the normal 220° F. and, therefore, enable the roller to retain heat for a substantially longer period of time. In addition, a cooler roller is achieved so that chances of severe burns is lessened.

Moreover, in the present embodiment, a hair roller heating system as shown in FIG. 5 for heating the hair rollers can be provided as an alternate heating source in addition to the capability of the rollers to be heated by microwaves. The fluid/air flow channel 30 may cooperate with an electrical heating element 40 used for heating conventional electrical rollers to supply heat to the roller.

As previously described, addition of more clay results in a slower heat up and more heat retention, whereas the elimination of amounts of clay results in a faster heat up and less heat retention. When arranged in layers, the inner microwave heatable layer heats rapidly, transferring heat through the outer microwave invisible layer at a much slower rate. This creates a heat transfer article with a core temperature substantially warmer than the outer layer. The actual characteristics are determined by the thickness and volume ratios of the inner microwave reactive layer and the outer non-microwave reactive layer. The outer layer acts as an insulator to slow the heat transmission from the inside of the element to the outside of the heat exchange element.

Other suitable articles and applications which may be employed using alternating microwave heatable and microwave invisible layers include therapeutic heating pads wherein one side of the pad is warmer than the opposite side. The warmer side is made of a layer of microwave-heatable clay/oil composition and the cooler side is made of a microwave-invisible clay/oil composition as described herein. Other articles may be produced using the layering arrangement described above and illustrated in FIG. 4.

The central fluid/air flow channel 30 arrangement illustrated in FIG. 6 and described above may be used in other applications to flow a fluid such as air or water therethrough to heat same. The microwave heatable layer immediately adjacent to the flowing water transfers heat to the fluid flowing therethrough and the insulating exterior microwave invisible layer provides sufficient insulation therefor.

It will be understood that the present invention is not limited to the particularly described clay/oil compositions but further includes various other clay/oil composition proportions which have been heat treated and which have not been heat treated. It should also be understood that the present invention is not limited to the specific compositions or processes described herein and that any composition having a formula equivalent to that described falls within the scope of the present invention. Preparation routes of the heat exchange mediums are merely exemplary so as to enable one of ordinary skill in the art to make the composition and use it according to the herein described processes. It will also be understood that while the form of the invention shown and described herein constitutes a preferred embodiment of the invention, it is not intended to illustrate all possible forms of the invention. The words used are words of description rather than of limitation. Various changes and variations may be made to the present invention without departing from the spirit and scope of the following claims.

What is claimed:

1. A heating element for providing extended transmission of heat or cold comprising a first encapsulated containment vessel housing a heat exchange medium comprising clay and oil and a second encapsulated containment vessel comprising a heat exchange medium comprising clay and oil, said heat exchange medium in said first encapsulated containment vessel and said heat exchange medium in said second encapsulated containment vessel having different thermal capabilities so that one of said heat exchange mediums absorbs heat faster than the other but the other of said heat exchange mediums retains heat for a longer period of time.

2. A heating element comprising a predetermined number of layers of containment vessels, wherein one of said containment vessels houses a first heat exchange medium comprising clay and oil, and another of said containment vessels houses a second heat exchange medium comprising clay and oil wherein said second medium has different thermal capabilities than said first medium so that said first medium absorbs heat at a different rate than said second medium.

3. A heating element as defined in claim 2 wherein at least one of said heat exchange mediums has been subjected to heat treatment.

4. A heating element as defined in claim 2 wherein said heating element is shaped into a hair roller design defining layers of containment vessels arranged about a channel concentrically disposed therein, said channel being capable of insertion about a conventional electric hair roller heating element for heating said heating element.

5. The heating element as defined in claim 2 wherein at least one of said heat exchange mediums is microwave-heatable.

6. The heating element as defined in claim 2 wherein both of said heat exchange mediums are microwave-heatable.

* * * * *